United States Patent [19]

Tayot et al.

[11] Patent Number: 4,764,279
[45] Date of Patent: Aug. 16, 1988

[54] PROCESS FOR PREPARING THE PRINCIPAL PROTEINS OF HEMOLYZED BLOOD IN THE NON-DENATURED FORM

[75] Inventors: Jean Louis Tayot, La Tour De Salvagny; Paule A. Gattel, Caluire; Michel A. Tardy, Lyon, all of France

[73] Assignee: Institut Merieux, Lyon, France

[21] Appl. No.: 874,788

[22] Filed: Jun. 13, 1986

Related U.S. Application Data

[63] Continuation of Ser. No. 628,284, Jul. 6, 1984, abandoned.

[30] Foreign Application Priority Data

Jul. 7, 1983 [FR] France ................................. 83 11323

[51] Int. Cl.$^4$ ...................... B01D 15/08; B01D 21/00
[52] U.S. Cl. .................................... 210/656; 210/730; 210/743; 436/63; 436/66; 436/175
[58] Field of Search ............... 210/635, 656, 927, 730, 210/743; 435/803; 436/86, 87, 88, 161, 175, 15, 16, 17, 63, 66; 260/112 B, 121

[56] References Cited

U.S. PATENT DOCUMENTS 3,637,489 1/1972 Haller .............................. 210/927 X
3,657,116 4/1972 Haller .................................. 210/656
4,297,274 10/1981 Bohn et al. ........................ 260/112 B

OTHER PUBLICATIONS

"Industrial Ion Exchange Chromatography of Proteins on DEAE Dextran Derivatives of Porous Silica Beds", Taylor et al. *Chromatogr. Synth. Biol. Polym.*, (1978), 2, pp. 95–110.

Primary Examiner—Richard V. Fisher
Assistant Examiner—W. Gary Jones
Attorney, Agent, or Firm—Larson and Taylor

[57] ABSTRACT

The process comprises subjecting the hemolyzed blood to a clarification step at a pH of between 4 and 6 in the presence of less than 15% of alcohol, then, after concentration, effecting a chromatography by exchange of anions so as to separate the hemoglobin, the albumin being thereafter eluted. The hemoglobin and the globulins may then be separated out by precipitation with 25% alcohol at a pH of 7. The proteins obtained are in the native state.

10 Claims, No Drawings

PROCESS FOR PREPARING THE PRINCIPAL PROTEINS OF HEMOLYZED BLOOD IN THE NON-DENATURED FORM

This application is a continuation of application Ser. No. 628,284 filed July 6, 1984, now abandoned.

The present invention relates to a process for separating the principal proteins from hemolyzed blood so as to produce on an industrial scale proteins such as albumin, haemoglobin and gamma-globulins.

Processes for fractionating on an industrial scale proteins from the plasma or the blood serum are based on selective precipitation methods. One of the processes, which is well known, is the Cohn process employing the selective precipitation with ethanol. Other processes use other chemical agents such as solvents, ammonium sulphate, caprylic acid, rivanol. These various processes have been mainly employed to obtain and purify albumin and gamma globulins.

However, they have a number of drawbacks, among which may be mentioned a limited selectivity and consequently the obtainment of a limited degree of purification, losses of yield by denaturation owing to the formation of polymers or protein aggregates during the precipitation steps, and fastidious, noisy and delicate industrial operations, such as the centrifuging operations, requiring skilled and competent personnel.

Further, as soon as these processes are employed on hemolyzed blood, for example placental blood which is the most important source of serum proteins, the known steps for eliminating the hemoglobin result in the denaturation of the latter. Now, it would be desirable to have large sources of native hemoglobin available owing in particular to the interest of haemoglobin as a source of artificial blood.

It has therefore already been envisaged to carry out steps for purifying proteins of plasma or hemolyzed blood by chromatography and, in particular ion exchange chromatography, by using modern chromatography supports, such as for example silica microballs coated with DEAE Dextran (see for example French Pat. No. 76 23176 filed on July 29, 1976).

It has consequently already been envisaged to subject to a chromatographic separation step the placental supernatant of albumin obtained after alcoholic precipitation of the $\gamma$-globulins at a pH of 6.8 in the presence of 25% of ethanol, thereby separating the hemoglobin from the albumin which was then recovered by elution with a 1% NaCl solution (see J. L. TAYOT et al.; Chromatography of synthetic and biological polymers, 1978, Vol. 2, pages 95 to 109). A similar process has also been suggested in said French patent in which the supernatant of the alcoholic precipitation of the mass of globulins is subjected to a chromatographic separation at a pH of between 6 and 7 after dilution in distilled water so as to reduce the concentration of alcohol and thereby make it possible to separate the albumin from the hemoglobin which travels through the column without being fixed to the support.

However, notwithstanding the advantages to be expected from the chromatographic separation, it was not possible to employ these haemolyzed blood purifying processes on an industriral scale.

It is true that it had already been proposed to purify the albumin of placental origin by chromatographic separation steps, but on the condition of first of all eliminating the main part of the hemoglobin by a denaturing precipitation, for example with chloroform (see J. L. TAYOT et al.; Cooperation internationale et derives sanguins-Talloires 1981; Ed. fondation MERIEUX), but such a process results in an irreversible denaturation of the hemoglobin. On the other hand, the aforementioned chromatographic separation operations on the supernatant of placental origin containing the albumin and the hemoglobin have not been able to attain the industrial stage, in particular owing to a slight fixing of the hemoglobin on the support which is difficult to elute completely so that the accumulation of the pigments, from cycle to cycle, on the support hinders the fixing capacity and the duration of use. Further, the solution injected into the column is very difficult to clarify. It is continuously cloudy, which renders the filtration very difficult. Moreover, it contains salts which strongly reduce the fixation of the albumin.

An object of the invention is therefore to overcome these drawbacks and to provide a process for separating the principal proteins from the hemolized blood in the nondenatured form, which is capable of separating, with an extremely high degree of purity, the principal proteins such as albumin, hemoglobin, and, if desired, $\gamma$-globulins.

Another object of the invention is to provide such a process which permits the cheap treatment of extremely large quantities of hemolyzed blood, such as for example several tons or several dozens of tons of placenta per day corresponding to several dozens of thousands of litres of hemolyzed blood.

The invention provides a process for separating the principal proteins from hemolyzed blood and in particular the albumin and the hemoglobin in the non-denatured state, comprising effecting a chromatographic separating step for separating the albumin and the hemoglobin wherein a hemolyzed blood is subjected to a clarifying step, and then, preferably before any alcoholic precipitation of $\gamma$-globulins, a chromatographic analysis of the hemolyzed blood is effected on an anionon exchanging chromatographic support at a pH higher than 4.8 and lower than 6.8, and preferably lower than 6 in the case of a prior alcoholic precipitation of the $\gamma$-globulins, the pH being preferably between 5 and 6, after which there are recovered separately the hemoglobin issuing from the chromatographic column and the albumin obtained after elution.

In a particularly preferred manner, the clarification is effected at a pH between 4 and 6, and preferably between 4.8 and 5.4, in the presence of alcohol, preferably ethanol, at a concentration below 15% and preferably in the neighbourhood of 8%.

As the haemolyzed blood is usually diluted, a concentrating step is employed and carried out on ultrafiltration systems having a cut-off threshold preferably of the order of 10,000 daltons, preferably in such manner as to concentrate at least four times the hemolyzed blood, and a diafiltration.

In the case which is not preferred and in which the hemolyzed blood has been previously subjected to alcoholic precipitation stages, in particular for the separation of the $\gamma$-globulins, it is necessary to effect a dilution in distilled water or like liquid in order to ensure that the alcohol content does not exceed 15%. This requires operating on very large volumes and moreover presents drawbacks due to the fact that the necessary additives in the case of alcoholic precipitation of the $\gamma$-globulins reduce the possibilities of adsorption of the chromatographic support.

If it is desired to separate the globulins and in particular the γ-globulins from the purified hemoglobin from which the albumin has been removed, it is possible, after having obtained this hemoglobin by the chromatographic step, to treat advantageously the filtrate with the addition of ethanol at about 25% in the cold state and with the pH adjusted to about 7. The immunoglobulin precipitate can then be recovered by centrifuging or filtration and then be subjected to the purifying operations which may be necessary. The corresponding supernatant or filtrate contains the hemoglobin in the practically pure native state. Preferably, this hemoglobin is diluted with at least one volume of distilled water so as to lower the concentration of ethanol sufficiently to avoid any subsequent denaturation. The solution may be subjected to an ultrafiltration and diafiltration operation to recover the concentrated native hemoglobin ready for the other purifying operations or other treatments necessary for its conversion into an artificial substitute for blood.

According to the invention, the chromatographic support is a support having very high mechanical properties and comprising for example a substrate of silica balls.

The chromatographic support is preferably the support named Spherodex and described for example in said French patent or in the Luxembourg patent No. 73 094 filed on July 29, 1975, consisting of a porous silica coated with DEAE Dextran and prepared in the MERIEUX Institute.

Further advantages and features of the invention will be apparent from the following description which is given merely by way of a nonlimiting example.

(1) Step for clarifying the hemolyzed placental blood 150 kg of human placentas are ground in the frozen state and dispersed in 150 liters of water to which 22 liters of ethanol are added so as to reach a temperature of 0° C. and an alcohol concentration of about 8%. The suspension obtained is vigorously agitated and then subjected to a filtration on a press having a volume of 400 liters and equipped with a gauze having a porosity of 50 microns, so as to separate the blood juice from the placental tissues. The recovered liquid occupies a volume of 270 liters. Acetic acid or N hydrochloric acid indifferently, is added to adjust the pH to 5.10 while stirring at 0° C. After waiting 2 hours, the suspension is injected at 300 l/h in a centrifuge. A precipitate in the neighbourhood of 7 to 10 kilograms which varies from day to day is eliminated. The blood obtained in the supernatant is perfectly clear and has a volume of about 260 liters.

(2) Step for concentration and diafiltration of the clarified blood

An ultrafilter equipped with a membrane having a cutoff threshold of 10000 daltons is used. For example, two spiral cartridges, each 5 meters square, sold by Millipore, are suitable for this operation. After concentration to about 60 liters, the pH is adjusted to 5.50 with N soda and the product is then diafiltered at constant volume with about 200 liters of demineralized water. The rate of elimination of the ultrafiltrate is about 50 l/h for a pressure of 4 bars at the inlet. The complete operation lasts about 8 hours at +4° C. The final pH is in the neighbourhood of 5.25 and is not modified. After regeneration, the ultrafilter can thus be used again more than 200 times without clogging.

After having been left for 15 hours at +4° C., the concentrated blood contains a slight precipitate of euglobulins which is eliminated by centrifuging. The deposit obtained represents a weight of 100 to 300 grams depending on the batches. The concentrated blood clarified with a volume of 120 liters is then filtered without problems on a membrane having a porosity of 0.2 μ and kept in the sterile state until the following step.

(3) Chromatographic separation step

A column having a diameter of 16 cm and a height of 1 m is filled with 9 kg of Spherodex. It is put in equilibrium with a phosphate buffer 0.01M pH 5.25 under the sterile conditions already described (TAYOT et coll.: Coopération Internationale et dérivés sanguins, 1981, Editions Fondation MERIEUX Lyon). The 120 liters of concentrated and filtered blood obtained previously are injected into a column at the rate of 40 l/h in a sterile manner through a filter having a porosity of 0.2 μ. The colume is then rinsed with 40 liters of buffer $PO_4$ 0.01M pH 5.25. The filtrate, 135 liters in volume, containing the hemoglobin and the immunoglobulins, has albumin completely removed therefrom. It is kept at +2° C. until the following step. The albumin fixed on the column with other proteins is then washed out by injection of 60 liters of a 20 g/l solution of NaCl. A volume of 50 liters is sufficient to recover quantitatively the albumin, namely about 1200 g (8 g/kg of placentas on average). This albumin solution must then be subjected to other known steps of purification so as to render it utilizable in human therapeutics.

After washing with a 0.1N solution of HCl and alcohol, the column is then ready for a new cycle of utilization.

More than 50 cycles were effected with the same column with no loss of effectiveness.

(4) Final separation of the gamma-globulins and the hemoglobin

The preceding filtrate (135 liters) is adjusted by sodium chloride 8 g/l, the pH is adjusted to 7 and the filtrate is cooled to 0° C. 45 liters of ethanol cooled to −20° C. are progressively added while stirring and the temperature is finally adjusted to −5° C. After having been left overnight, the suspension obtained is centrifuged at the rate of 300 l/h.

The gammaglobulin precipitate obtained weighs on average 900 g for several batches, and must then be subjected to other purification operations already known so as to prepare immunoglobulins which may be used in human therapeutics.

The supernatant obtained is perfectly clear. It contains the hemoglobin from which the immunoglobulins have been practically removed. It is diluted with 300 liters of water at 0° C. so as to bring the concentration of alcohol to below 10%. This solution is concentrated by ultrafiltration on the same module described before and can be finally diafiltered so as to adjust the ionic force and the composition of the solution in accordance with its future utilization. The quantity of hemoglobin obtained is 3,700 g, namely a yield of around 25 g/kg placentas.

Tests carried out at a pH of 5.0 reveal a reduction in the capacity of the column to retain the albumin, while at a pH of 5.2 the albumin is totally retained. Tests carried out with a pH of 6.5 reveal that, although the albumin is fully retained, a contamination of the support by the pigments of the hemoglobin starts to appear.

In the nonpreferred case in which the hemolyzed blood is subjected to an alcoholic precipitation at a pH of 7 for separating the γ globulins, the clarification step at a pH 5.1 and with 8% alcohol is carried out before and/or after the precipitation of the globulin fraction.

What is claimed is:

1. A process for separating hemoglobin, γ-globulins and albumin from hemolyzed blood, comprising subjecting said hemolyzed blood to a clarification step comprising contacting said hemolyzed blood at a pH of between 4 and 6 with alcohol at a concentration that does not exceed 15% and eliminating the precipitate which is obtained, then effecting an anion exchange chromatography of the clarified hemolyzed blood containing hemoglobin, γ-globulin and albumin in a chromatographic column on an anion exchanging chromatographic support at a pH higher than 4.8 and lower than 6.8, thereafter separately recovering hemoglobin including γ-globulins issuing from the chromatographic column as filtrate and albumin by elution.

2. A process according to claim 1, comprising effecting the chromatography at a pH of between 5 and 6.

3. A process according to claim 1, comprising effecting the clarification at a pH of between 4.8 and 5.4.

4. A process according to claim 1, comprising effecting the clarification step in the presence of alcohol at a concentration of about 8%.

5. A process according to claim 1, comprising effecting the clarification step in the presence of ethanol.

6. A process according to claim 1, comprising separating the γ-globulins from the recovered hemoglobin.

7. A process according to claim 6, comprising separating the γ-globulins by precipitation with alcohol at about 25% and with a pH in the region of 7.

8. A process according to claim 1, comprising employing for the chromatography a support of porous silica coated with DEAE Dextran.

9. A process according to claim 1, comprising equilibrating the chromatographic column with an 0.01M phosphate buffer, then rinsing the column in the same buffer, the albumin being eluted with a 20 g/l solution of NaCl.

10. A process for separating hemoglobin and albumin from a hemolyzed blood from which γ-globulins have been separated by submitting said hemolyzed blood to an alcoholic γ-globulins separation step comprising subjecting said hemolyzed blood to a clarification step which comprises diluting said hemolyzed blood to an alcohol content that does not exceed 15%, at a pH of between 4 and 6 and eliminating the precipitate which is obtained, then effecting an anion exchange chromatography of the clarified hemolyzed blood containing hemoglobin and albumin in a chromatographic column on an anion exchanging chromatographic support at a pH higher than 4.8 and lower than 6.8, thereafter separately recovering hemoglobin issuing from the chromatographic column as filtrate and albumin by elution.

* * * * *